United States Patent
Gudlavalleti

(10) Patent No.: US 11,851,645 B2
(45) Date of Patent: Dec. 26, 2023

(54) PAPQUIN-50 A QUINOA GRAIN-BASED BACTERIAL GROWTH MEDIUM NITROGEN SOURCE

(71) Applicant: Seshu Kumar Gudlavalleti, Holly Springs, NC (US)

(72) Inventor: Seshu Kumar Gudlavalleti, Holly Springs, NC (US)

( * ) Notice: Subject to any disclaimer, the term of this patent is extended or adjusted under 35 U.S.C. 154(b) by 133 days.

(21) Appl. No.: 17/583,067

(22) Filed: Jan. 24, 2022

(65) Prior Publication Data
US 2023/0235273 A1 Jul. 27, 2023

(51) Int. Cl.
*C12N 1/20* (2006.01)
*C12P 21/06* (2006.01)

(52) U.S. Cl.
CPC ..................................... *C12N 1/20* (2013.01)

(58) Field of Classification Search
CPC ... C12N 1/20; C12R 2001/36; C12R 2001/46; C12P 21/06
See application file for complete search history.

(56) References Cited

PUBLICATIONS

Yu D. et al., English translation of CN 112826781 A; May 25, 2021—"Preparing Quinoa Extract With Anti-wrinkle And Anti-aging Effects Used In Cosmetic, By Extracting Quinoa Extract From Quinoa, Enzymatically Hydrolyzing Quinoa Extract With Protease, And Separating Enzymatic Hydrolyzate", Total 2 pages. (Year: 2021).*

Dallagnol A. M. et al., "Fermentation of quinoa and wheat slurries by Lactobacillus plantarum CRL 778: proteolytic activity", Appl. Microbiol. Biotechnol., (2013), vol. 97, pp. 3129-3140, (DOI 10.1007/s00253-012-4520-3). (Year: 2013).*

* cited by examiner

*Primary Examiner* — Satyendra K Singh

(57) ABSTRACT

Commercially available Quinoa grain powder is subjected to proteolytic digestion using papain enzyme. Derived hydrolysate is ultrafiltered using two sequential ultrafiltration steps of 50 KDa and 5 KDa membranes to remove high and low molecular impurities respectively. Concentrated filtrate is 0.2 µ filter-sterilized and used as a component growth medium for fastidious microorganisms *Neisseria meningitidis* and *Streptococcus pneumoniae*. The product is tested for its ability to be used as meat free nitrogen and carbon source for the fastidious bacterial growth and found to be working well.

2 Claims, No Drawings

PAPQUIN-50 A QUINOA GRAIN-BASED BACTERIAL GROWTH MEDIUM NITROGEN SOURCE

BACKGROUND OF THE INVENTION

1. Field of Invention

The current invention is related to the fields of Medical Microbiology, Industrial Microbiology, Biotechnology, and Bacterial Vaccine Manufacturing.

2. Description of the Prior Art

Purified extracts from meat [example: Beef extract, peptones] and animal products such as milk derived casein enzyme hydrolysates [example: Casein hydrolysate], yeast cell extracts [example: Yeast extract] and plant origin seed extracts [example: Hy-Soy] have been used as nitrogen and/or carbon sources in microbial growth media formulations Peptones are derived from meat or milk and Tryptones are derived from only milk. A mixture of animal origin pancreatic digestive enzymes amylase, lipase and protease called 'pancreatin' is used for meat or milk protein casein hydrolysis to produce peptones and tryptones respectively. Different varieties of Soya bean protein-based enzyme hydrolysates Peptone Hy-Soy, Peptone N—Z-Soy and Soy protein acid hydrolysates are already existing as commercial products. Water soluble, acid hydrolysates, enzymatic hydrolysates of above sources are often proven their promising role in bacterial growth media. Commercial bacterial fermentations are widely taking place in pharmaceutical industries not only to produce different components including antigens from cultured microbes but also to express recombinant proteins in them. Commercial fermentation media formulations are demanding the importance of plant-based components because of animal component related health issues for example, bovine spongiform encephalopathy in cattle. A search for highly nutritious plant-based products is currently growing more than ever. Growth of fastidious microbes is dependent on specific nutrient growth factors of the medium. Yeast (extract) is generally recognized as safe (GRAS) by USFDA and widely used currently in bio-pharma fermentation media. However, there are many issues associated with yeast extract of lot-to-lot variation that causes batch to batch fermentation growth and yield variations. Yeast extracts are produced by culturing source organism ex. *Saccharomyces cerevisiae* using molasses in fermentation media. Grown yeast cells are lysed in multiple ways including, mechanical, non-mechanical, invasive, or non-invasive ways. These process variabilities can cause variations on the composition of yeast extract product. Plant derived growth supplements can pose lesser processing variability and hence can be more consistent in their batch fermentation performance. Quinoa is common name for *Chenopodium quinoa* a small flowering plant of family Amaranthaceae. Quinoa seed (grain) a pseudo-cereal is edible that comes in various colors, mainly white, yellow, red, and black. More than 120 known varieties of quinoa are available. Quinoa grain is gluten-free high protein source containing all essential amino acids, magnesium, B-vitamins, iron, potassium, calcium, manganese, phosphate and vitamin E. The plant has been cultivated for more than 5000 years and indigenous to the Andean region of South America. It had been introduced in Europe, North America, Asia, and Africa recently. Quinoa fluor contains nearly 16% protein while white wheat flour contains a 10% protein. Quinoa seed is a naturally gluten-free and fluor is used widely in human food consumption as healthy protein source for celiac patients. Quinoa beer was developed by de Meo et al (2011).

Quinoa flour slurry was recently used as medium component in lactic acid bacterial fermentation (Dallagnol A M et al. 2013).

REFERENCES

De Meo B, Freeman G, Marconi O, Booer C, Perretti G, Fantozzi P, (2011) Behaviour of malted cereals and pseudo-cereals for gluten-free beer production. J Inst Brew 117:541-546.

Dallagnol A M, Pescuma M, Valdez G F D, and Rollan G (2013) Fermentation of quinoa and wheat slurries by *Lactobacillus plantarum* CRL 778: proteolytic activity. Appl Microbiol Biotechnol 97(7):3129-3140.

BRIEF SUMMARY OF THE INVENTION

Plant based microbial growth media components are gradually replacing animal derived components. Quinoa seed grain powder (flour) is rich in proteins, carbohydrates, vitamins, and minerals. This invention, describes a method of preparing plant based quinoa flour medium component, digestion by using plant based enzyme papain, extraction and purification procedure. Commercially available quinoa powder [Bob's Red Mill Organic Quinoa Flour] was subjected to papain enzymatic hydrolysis. A 50 KDa molecular weight cut-off [MWCO] cassette membrane ultrafiltered, derived hydrolysate permeate named herein as PapQuin-50 was tested for its suitability on fastidious bacterial growth. w Papain also known as papaya proteinase, is a cysteine protease that cleaves peptide bonds of basic amino acids, leucine, or glycine. Papain pH optimum is 6.0-7.0 and the temperature optimum is 60-70° C. It also hydrolyzes esters and amides. Papain digests most protein substrates more extensively than pancreatic proteases.

Source of the quinoa flour must be identified/secured for batch consistency of the product. In this submission a commercially available organic quinoa powder is used.

Derived hydrolysate is ultrafiltered using 50 KDa MWCO membrane cassette to remove high-molecular impurities including the saponins and permeate was collected. The permeate is then purified by 5 KDa MWCO membrane ultrafiltration to collect retentate. Concentrated retentate is 0.2μ filter-sterilized and used as growth medium for fastidious microorganisms *Neisseria meningitidis* and *Streptococcus pneumoniae*. The product is tested for its ability to be used as meat free nitrogen and carbon source for the fastidious bacterial growth and found to be working well.

DETAILED DESCRIPTION OF THE PREFERRED EMBODIMENT

Process used in the current invention:

Water solubilized quinoa powder is prepared at a concentration of 50 mg/ml by constant mixing at 37° C. for 2 to 3 h. The solution is then filtered through 0.8 μm filter to separate undissolved portion.

Filtered Quinoa solution is then pH adjusted to 7.0 and treated with papain [Thermo Scientific Cat #AC416761000] enzyme at a final concentration of 50 μg/ml at 65° C. for 6 h with constant shaking in a shaker incubator at 150 RPM.

- Centrifuged the hydrolysate at 8000 g at 4° C. for 30 minutes to separate any insoluble sediment.
- Transferred the supernatant to ultrafiltration step in a Viva-flow [Sartorius item #VF05P3] 50 KDa MWCO PES membrane cassette on a laboratory scale cross flow system.
- Collected the flow-though (Permeate) at a twice starting concentration (100 mg/ml) based on collected flow-through volume.
- The Permeate is further purified with Viva-flow [Sartorius item #VFO5P1] 5 KDa MWCO membrane cassette ultrafiltration system for 5 diafiltration-volumes of purified water to remove small molecular contamination to collect the retentate.
- 0.2 micron Filter sterilized product PapQuin-50 was used as a medium component substituting yeast extract in Frantz medium of composition given below table 1.
- Tested the medium agar plates and liquid growth for fastidious organism *Neisseria meningitidis* serogroups A, C, W-135 and Y and *Streptococcus pneumoniae* serotypes 7F, 9V, 12F and 23F. 15 g/L Bacto agar is used for making agar plates.
- Results showed that Papquin-50 can replace yeast extract in Frantz medium to support the agar plate and liquid medium growth of *Neisseria meningitidis* and *Streptococcus pneumoniae* strains used.

TABLE 1

Medium composition: Frantz medium replacing Yeast extract with PapQuin-50

| Component | *Frantz media g/L | Current-work medium g/L |
|---|---|---|
| L-glutamic acid | 1.60 | 1.60 |
| L-Cysteine · HCl | 0.02 | 0.02 |
| NaCl | 6.00 | 6.00 |
| $Na_2HPO_4$, $12H_2O$ | 6.24 | 6.24 |
| KCl | 0.09 | 0.09 |
| $NH_4Cl$ | 1.25 | 1.29 |
| $MgSO_4$, $7H_2O$ | 1.23 | 1.23 |
| Glucose | 5.00 | 5.00 |
| PapQuin-50 | — | 2.00 |
| Yeast Extract | 2.00 | — |

Frantz I. D. Jr Growth Requirements of the meningococcus. J. Bact (1942). 43:757-761, 1

Results:

- Papquin-50 used to replace the yeast extract in Frantz medium worked very well for both *Neisseria* and *Streptococcus* strains used.
- Papquin-50 is shown to be working for agar plate growth and liquid medium growth during the invention.

CONCLUSIONS

Plant origin papain enzyme digested quinoa flour nitrogen source named 'PapQuin-50' preparation is described in this patent application. Commercially available Quinoa grain powder used in this claim is digested with commercially available plant origin enzyme papain. A MWCO 50 KDa and 5 KDa membrane diafiltration steps are used to purify this nitrogen source to make consistent preparation. Growth promoting activity of the PapQuin-50 medium replacing yeast extract in a standard medium supporting fastidious Gram negative (meningococci) and Gram positive (Pneumococci) bacteria has been presented. This nutritious medium supplement Papquin-50 may support the growth of other bacterial species as well.

The invention claimed is:

1. A growth medium composition for growing fastidious bacteria *Neisseria meningitidis* and *Streptococcus pneumoniae*, the growth medium comprising an ultrafiltration fraction of a quinoa grain papain hydrolysate in the molecular weight range of 5 kDa to 50 kDa, wherein said ultrafiltration fraction is supplemented at a concentration of 2 g/L to a bacterial growth medium lacking yeast extract to form said growth medium composition that supports the growth of the fastidious bacteria *Neisseria meningitidis* and *Streptococcus pneumoniae.*

2. A method for preparing a growth medium composition comprising quinoa grain papain hydrolysate comprising an ultrafiltration fraction in the molecular weight range of 5 kDa to 50 kDa for growing fastidious bacteria *Neisseria meningitidis* and *Streptococcus pneumoniae*, the method comprising the steps of:

i) performing enzymatic hydrolysis of an aqueous solution of quinoa grain powder by papain to obtain a quinoa grain papain hydrolysate, ii) performing purification of the papain hydrolysate using sequential ultrafiltration steps with membranes having 50 kDa molecular weight cutoff (MWCO) followed by 5 kDa MWCO membrane filtration to obtain a retentate, iii) filter sterilizing said retentate to obtain the quinoa grain papain hydrolysate comprising the ultrafiltration fraction in the molecular weight range of 5 kDa to 50 kDa, and iv) adding the sterilized retentate to a bacterial growth medium that does not comprise yeast extract, at a concentration of 2 g/L, to prepare the growth medium composition comprising the quinoa grain papain hydrolysate.

* * * * *